(12) United States Patent
Blewett et al.

(10) Patent No.: US 6,428,538 B1
(45) Date of Patent: Aug. 6, 2002

(54) APPARATUS AND METHOD FOR THERMAL TREATMENT OF BODY TISSUE

(75) Inventors: Jeffrey J. Blewett, Plantsville; Christopher W. Maurer, Newtown, both of CT (US)

(73) Assignee: United States Surgical Corporation, Norwalk, CT (US)

( * ) Notice: Subject to any disclaimer, the term of this patent is extended or adjusted under 35 U.S.C. 154(b) by 0 days.

(21) Appl. No.: 09/546,591

(22) Filed: Apr. 11, 2000

Related U.S. Application Data

(63) Continuation of application No. 08/733,856, filed on Oct. 18, 1996, now abandoned.
(60) Provisional application No. 60/005,741, filed on Oct. 20, 1995.

(51) Int. Cl.[7] ................................................. A61B 18/18
(52) U.S. Cl. ............................ 606/46; 606/47; 606/41; 607/101
(58) Field of Search ................ 606/41–52; 607/97–102, 607/156; 600/156

(56) References Cited

U.S. PATENT DOCUMENTS

| | | |
|---|---|---|
| 3,991,770 A | 11/1976 | LeVeen |
| 4,011,872 A | 3/1977 | Komiya |
| 4,121,592 A | 10/1978 | Whalley |
| 4,154,246 A | 5/1979 | LeVeen |
| 4,237,898 A | 12/1980 | Whalley |
| 4,280,503 A | 7/1981 | Ackerman |
| 4,311,154 A | 1/1982 | Sterzer et al. |
| 4,411,266 A | 10/1983 | Cosman |
| 4,423,727 A | 1/1984 | Widran et al. |
| 4,448,198 A | 5/1984 | Turner |
| 4,503,855 A | 3/1985 | Maslanka |
| RE32,057 E | 12/1985 | LeVeen |
| RE32,066 E | 1/1986 | LeVeen |
| 4,565,200 A | 1/1986 | Cosman |
| 4,601,296 A | 7/1986 | Yerushalmi |

(List continued on next page.)

FOREIGN PATENT DOCUMENTS

| | | |
|---|---|---|
| DE | 3247793 | 7/1983 |
| DE | 2941060 | 4/1990 |
| EP | 0608609 | 8/1994 |
| GB | 2119253 | 11/1983 |
| JP | 2121675 | 5/1990 |
| WO | 9004365 | 5/1990 |
| WO | 9103996 | 4/1991 |
| WO | 9116859 | 11/1991 |
| WO | 9210142 | 6/1992 |
| WO | 9220290 | 11/1992 |
| WO | 9304727 | 3/1993 |
| WO | 9315664 | 8/1993 |
| WO | 9513027 | 5/1995 |
| WO | 9706857 | 2/1997 |

*Primary Examiner*—Linda C. M. Dvorak
*Assistant Examiner*—David M. Ruddy

(57) ABSTRACT

An apparatus and method for the thermal treatment of tissue, e.g., prostatic tissue, with RF energy is disclosed. The apparatus includes a handle dimensioned to be grasped with a single hand of a surgeon, an elongated portion extending distally from the handle and defining a longitudinal axis, at least one electrode extending within the elongated portion and movable between a non-deployed position and a fully deployed position, and a trigger mechanism associated with the handle and having a trigger operatively connected to the one electrode. The trigger is movable to selectively and incrementally move the one electrode between the non-deployed position and the fully deployed position. A ratchet mechanism permits movement of the trigger in one direction corresponding to movement of the one electrode toward the fully deployed position while preventing movement of the trigger in a second direction. The elongated portion of the apparatus may be rotatable about the longitudinal axis to reposition the one electrode.

24 Claims, 13 Drawing Sheets

U.S. PATENT DOCUMENTS

| | | |
|---|---|---|
| 4,658,836 A | 4/1987 | Turner |
| 4,676,258 A | 6/1987 | Inokuchi et al. |
| 4,763,671 A | 8/1988 | Goffinet |
| 4,805,616 A | 2/1989 | Pao |
| 4,823,791 A | 4/1989 | D'Amelio et al. |
| 4,896,671 A | 1/1990 | Cunningham et al. |
| 4,907,589 A | 3/1990 | Cosman |
| 4,917,082 A | 4/1990 | Grossi et al. |
| 4,920,978 A | 5/1990 | Colvin |
| 4,950,267 A | 8/1990 | Ishihara et al. |
| 4,955,377 A | 9/1990 | Lennox et al. |
| 4,966,597 A | 10/1990 | Cosman |
| 4,979,948 A | 12/1990 | Geddes et al. |
| 5,007,908 A | 4/1991 | Rydell |
| 5,057,107 A | 10/1991 | Parins et al. |
| 5,078,716 A | 1/1992 | Doll |
| 5,083,565 A | 1/1992 | Parins |
| 5,084,044 A | 1/1992 | Quint |
| 5,098,431 A | 3/1992 | Rydell |
| 5,151,100 A | 9/1992 | Abele et al. |
| 5,159,925 A | 11/1992 | Neuwirth et al. |
| 5,169,397 A | 12/1992 | Sakashita et al. |
| 5,186,181 A | 2/1993 | Franconi et al. |
| 5,191,883 A | 3/1993 | Lennox et al. |
| 5,192,280 A | 3/1993 | Parins |
| 5,197,963 A | 3/1993 | Parins |
| 5,220,927 A | 6/1993 | Astrahan et al. |
| 5,246,438 A | 9/1993 | Langberg |
| 5,249,585 A | 10/1993 | Turner et al. |
| 5,273,524 A | 12/1993 | Fox et al. |
| 5,282,799 A | 2/1994 | Rydell |
| 5,290,286 A | 3/1994 | Parins |
| 5,293,878 A | 3/1994 | Bales et al. |
| 5,295,955 A | 3/1994 | Rosen et al. |
| 5,300,068 A | 4/1994 | Rosar et al. |
| 5,301,687 A | 4/1994 | Wong et al. |
| 5,304,214 A | 4/1994 | DeFord et al. |
| 5,318,563 A | 6/1994 | Malis et al. |
| 5,324,254 A | 6/1994 | Phillips |
| 5,330,518 A | 7/1994 | Neilson et al. |
| 5,334,193 A | 8/1994 | Nardella |
| 5,341,807 A | 8/1994 | Nardella |
| 5,342,357 A | 8/1994 | Nardella |
| 5,354,296 A | 10/1994 | Turkel |
| 5,364,392 A | 11/1994 | Warner et al. |
| 5,366,476 A | 11/1994 | Noda |
| 5,368,591 A | 11/1994 | Lennox et al. |
| 5,370,675 A | 12/1994 | Edwards et al. |
| 5,383,876 A | 1/1995 | Nardella |
| 5,383,917 A | 1/1995 | Desai et al. |
| 5,385,544 A | 1/1995 | Edwards et al. |
| 5,401,274 A | 3/1995 | Kusunoki |
| 5,403,311 A | 4/1995 | Abele et al. |
| 5,409,006 A | 4/1995 | Buchholtz et al. |
| 5,409,453 A | 4/1995 | Lundquist et al. |
| 5,413,588 A | 5/1995 | Rudie et al. |
| 5,421,819 A | 6/1995 | Edwards et al. |
| 5,423,808 A | 6/1995 | Edwards et al. |
| 5,431,649 A | 7/1995 | Mulier et al. |
| 5,435,805 A | 7/1995 | Edwards et al. |
| 5,437,662 A | 8/1995 | Nardella |
| 5,441,498 A | 8/1995 | Perkins |
| 5,454,782 A | 10/1995 | Perkins |
| 5,458,597 A | 10/1995 | Edwards et al. |
| 5,464,437 A | 11/1995 | Reid et al. |
| 5,464,445 A | 11/1995 | Rudie et al. |
| 5,470,308 A | 11/1995 | Edwards et al. |
| 5,470,309 A | 11/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,507,743 A | 4/1996 | Edwards et al. |
| 5,509,929 A | 4/1996 | Hascoet et al. |
| 5,514,130 A | 5/1996 | Baker |
| 5,531,676 A | 7/1996 | Edwards et al. |
| 5,531,677 A | 7/1996 | Lundquist et al. |
| 5,536,240 A | 7/1996 | Edwards et al. |
| 5,540,655 A | 7/1996 | Edwards et al. |
| 5,540,681 A | 7/1996 | Strul et al. |
| 5,542,915 A | 8/1996 | Edwards et al. |
| 5,542,916 A | 8/1996 | Hirsch et al. |
| 5,545,161 A | 8/1996 | Imran |
| 5,599,294 A | 2/1997 | Edwards et al. |
| 5,599,345 A | 2/1997 | Edwards et al. |
| 5,599,346 A | 2/1997 | Edwards et al. |
| 5,624,452 A | 4/1997 | Yates |
| 5,849,011 A | 12/1999 | Jones et al. |
| 6,022,334 A * | 2/2000 | Edwards et al. ............. 607/98 |
| 6,179,836 B1 * | 1/2001 | Eggers et al. ................. 606/45 |

\* cited by examiner

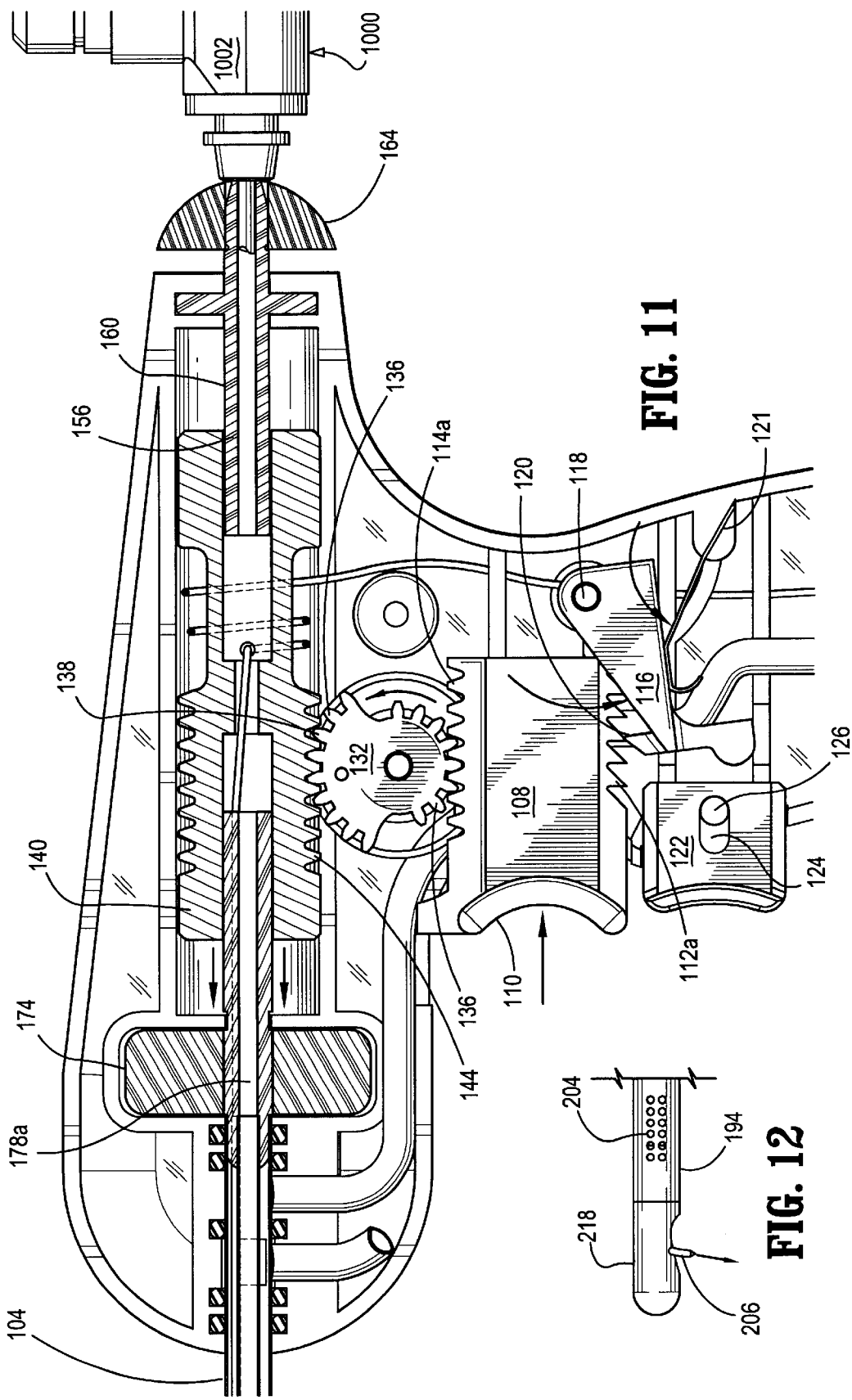

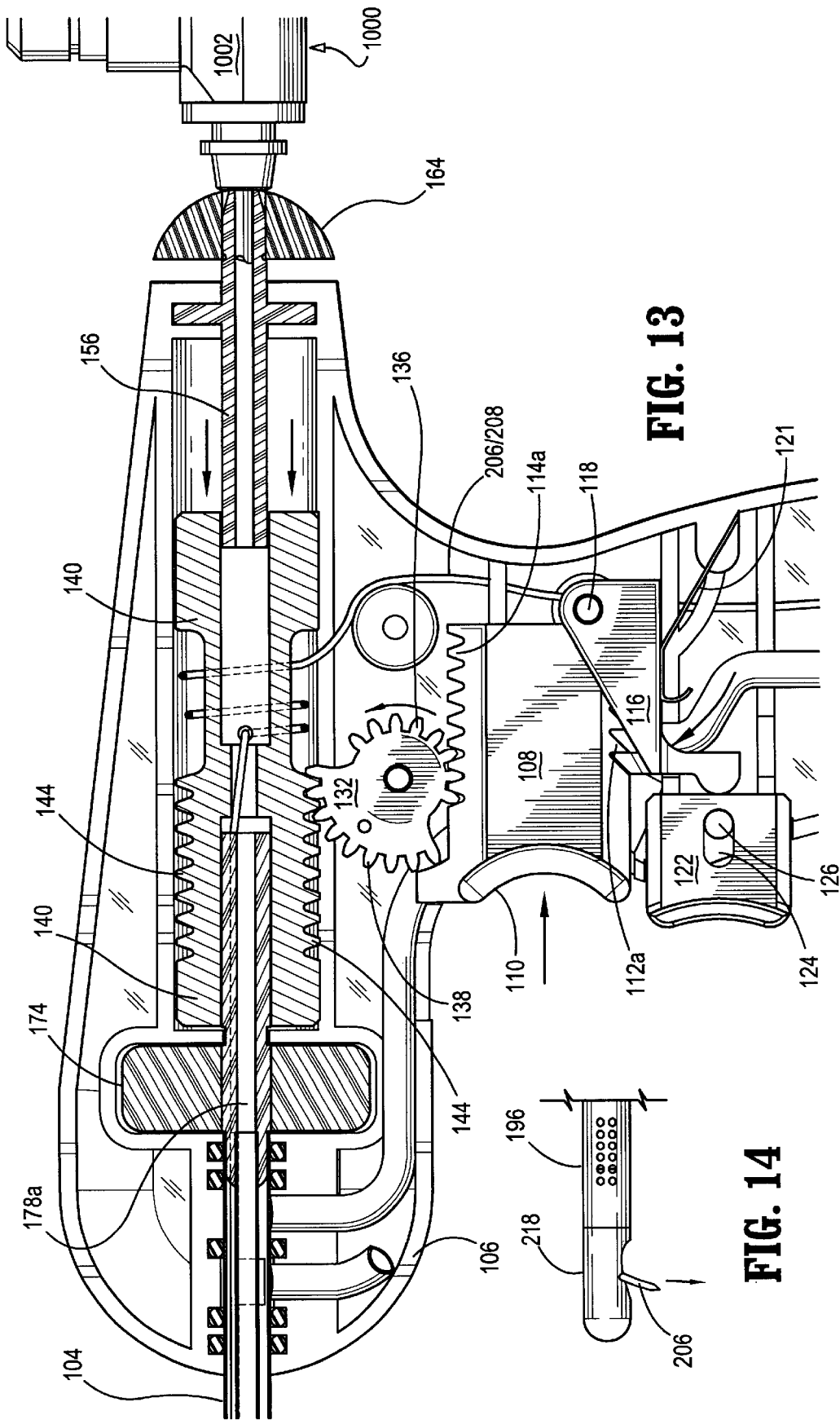

APPARATUS AND METHOD FOR THERMAL TREATMENT OF BODY TISSUE

This application is a continuation of application Ser. No. 08/733,856, filed Oct. 18, 1996, now abandoned, which claims priority to provisional application Ser. No. 60/005,741, filed Oct. 20, 1995.

BACKGROUND

1. Technical Field

The present disclosure relates generally to a method and apparatus for thermal treatment of tissue, and, more particularly, to a method and apparatus for the hyperthermia treatment of prostatic tissue.

2. Description of Related Art

Benign prostate hyperplasia (BPH) or hyperplasia affects over one out of every two males over the age of fifty. BPH is the non-cancerous enlargement of the prostate gland and is characterized generally by a constriction of the urethra by the prostate gland. An array of symptoms are associated with BPH including frequent urination, difficulties in urinary flow and associated pain.

Generally there are two primary methods for treating BPH, namely, drug therapy and surgical intervention. Drug therapy incorporates the use of one or more drugs such as Proscar™ and Hydrin™ to either reduce the size of the prostate or to relax the urethral muscles thereby facilitating the normal functioning of the urinary system. Known drug therapies, however, are limited in their effectiveness and present many drug side effect concerns.

Surgical methods for treating BPH include transurethral resection of the prostate (TURP), transurethral incision of the prostate (TUIP), visual laser assisted prostatectomy (VLAP), balloon dilation and stenting. TURP is the most common method employed for BPH treatment today and involves the insertion of an electrosurgical cutting instrument through the urethral passage. The cutting elements of the instrument are positioned adjacent the prostate gland, and the instrument is energized such that the cutting elements selectively cauterize and resect tissue from the core of the prostate. The TURP procedure, however, has many side effects including bleeding, electrograde ejaculation, impotence, incontinence, edema and a prolonged recovery period for the patient. An example of an electrosurgical cutting instrument utilized in conjunction with a TURP procedure is disclosed in U.S. Pat. No. 5,192,280.

Transurethral incision of the prostate (TUIP) involves the use of an electrocautery device which is passed through the urethra. The device is employed to make multiple incisions in the prostate, thereby permitting the prostate to be displaced from the urethra wall to create an opening for urine flow. Success with the TUIP procedure is generally limited providing only temporary relief and requiring a subsequent repeat of the procedure in the future.

Visual laser assisted prostatectomy (VLAP) includes insertion of a laser catheter through the urethra and directing laser energy laterally through the catheter sleeve at the urethral wall and the prostatic tissue. The laser energy causes the tissue to coagulate. The coagulated tissue eventually necrosis from lack of blood flow and is naturally removed from the body. Drawbacks of VLAP include increased recovery time, acute pain and irritation, and undesired burning of the urethral wall. Examples of methods and apparatuses utilized in VLAP treatment of BPH are disclosed in U.S. Pat. No. 5,242,438 to Saadatmanesh et al. and U.S. Pat. No. 5,322,507 to Costello.

Balloon dilation procedures for BPH involve expanding and stretching the enlarged prostate with a balloon catheter to relieve pressure off the constricted urethra while stenting incorporates the insertion of tiny wire-mesh coils which expand into a scaffold to hold the urethra open. Balloon dilation and stenting, however, are only temporary procedures typically requiring follow up within a year period. In addition, stenting presents complications of stent migration and consequent irritation.

More recently, two new surgical developments, namely, transurethral microwave therapy (TUMT) and high intensity focused ultrasound (HIFU) have been developed for the treatment of BPH. In accordance with a TUMT procedure, a foley-type urethral catheter having a microwave emitting antenna at a probe end is inserted into the urethral passage for a period of time sufficient to treat the tissue by microwave radiation. Intraurethral applications of this type are described in U.S. Pat. Nos. 4,967,765, 5,234,004 and 5,326,343. The drawbacks of TUMT include the inability to focus the heat energy in the prostatic area and the inability to achieve high temperatures uniformly within the prostate.

High intensity focused ultrasound (HIFU) includes directing high intensity ultrasound waves at the prostate tissue to create heat in a precise area to coagulate and necrose tissue. A transurethral probe is utilized to create the ultrasound beams for both imaging and ablation of the prostatic tissue. Disadvantages of this procedure include the inability to directly focus the ultrasound energy at the prostatic tissue.

A more recent and encouraging form of treatment for BPH involves thermally treating prostatic tissue with radiofrequency electromagnetic energy. For example, one current technique, known as transurethral needle ablation (TUNA™), involves the transurethral application of a medical probe having a pair of monopolar RF needle electrodes at its distal end The probe is inserted into the urethra and advanced to a position adjacent the prostate. Thereafter, the RF needles are advanced to penetrate the urethral wall and access the prostatic tissue. A RF current is transmitted through each electrode and passes through the tissue to a grounding pad to form a necrotic legion which is eventually reabsorbed by the body. Apparatuses and methods for treating BPH with RF energy are disclosed in U.S. Pat. Nos. 5,366,490; 5,370,675; 5,385,544; 5,409,453 and 5,421,819.

Although the use of RF electromagnetic energy in treating BPH shows promise in effectively and permanently alleviating symptoms of BPH, there exists significant limitations in the current state of development of RF thermal treatment and instrumentation.

SUMMARY

Accordingly, the present disclosure is directed to an apparatus and method for the thermal treatment of tissue, e.g., prostatic tissue, with RF energy. The apparatus permits enhanced control over deployment of the energy emitting electrodes to enable the surgeon to selectively focus and maintain the electromagnetic energy within a predetermined heating pattern thereby reducing the amount of damage to neighboring healthy tissue.

In one preferred embodiment, the apparatus for thermal treatment of tissue includes a handle dimensioned to be grasped with a single hand of a surgeon, an elongated portion extending distally from the handle and defining a longitudinal axis, at least one electrode extending within the elongated portion and movable between a non-deployed position and a fully deployed position, and a trigger mechanism associated with the handle and having a trigger operatively connected to the one electrode. The trigger is movable relative to the handle to selectively and incrementally move the one electrode between the non-deployed position and the fully deployed position. A ratchet mechanism is associated with the trigger mechanism to permit movement of the trigger in one direction corresponding to movement of the one electrode toward the fully deployed position and maintain the electrode in position while preventing movement of the trigger in a second direction. The ratchet mechanism may be selectively released by a release trigger which is mounted to the handle and operatively connected to the ratchet mechanism. The release trigger is movable to release the ratchet mechanism to thereby permit movement of the trigger in a second direction corresponding to movement of the one electrode to the non-deployed position.

In another preferred embodiment, the elongated portion of the apparatus is rotatable about the longitudinal axis to position the one electrode at a predetermined angular orientation with respect to the longitudinal axis. A rotatable control knob is associated with the handle and operatively connected to the elongated portion to impart rotational movement to the elongated portion. Irrigation conduits for supplying irrigation fluids for flushing and/or cooling of the tissue and an aspiration conduit may also be provided.

BRIEF DESCRIPTION OF THE PREFERRED EMBODIMENTS

Preferred embodiment(s) of the disclosure are described herein with reference to the drawings wherein:

FIG. 11 is an enlarged side cross-sectional view of the handle illustrating the drive trigger partially depressed to advance the drive collar and partially deploy the electrodes;

FIG. 12 is a side view of the distal end portion of the elongated member illustrating partial deployment of the electrodes when the drive trigger is in the position of FIG. 11;

FIG. 13 is a view similar to the view of FIG. 11 illustrating the drive trigger fully depressed corresponding to full deployment of the electrodes;

FIG. 14 is a view similar to the view of FIG. 12 illustrating the electrodes fully deployed;

Figure 17:
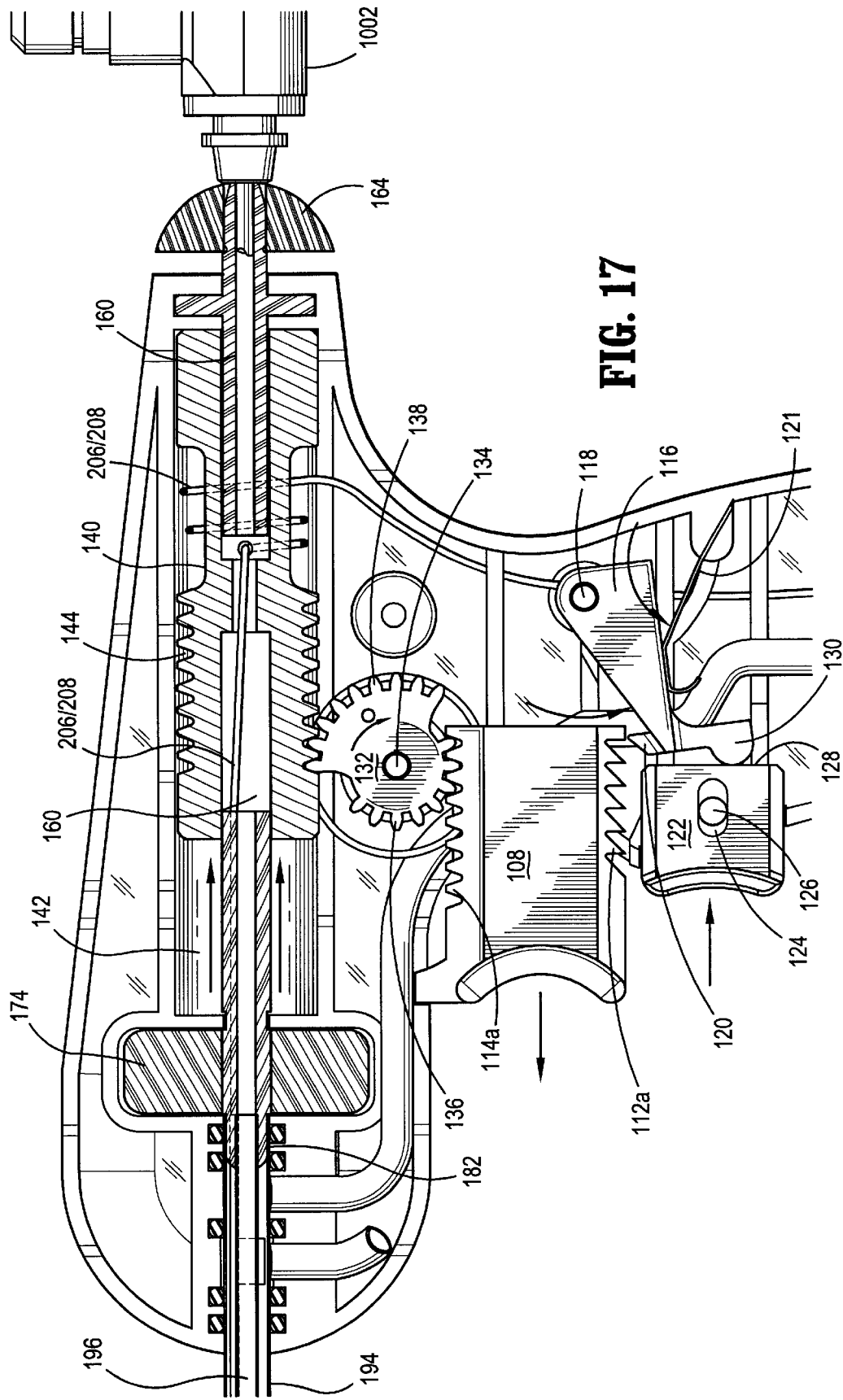
Figure 18:
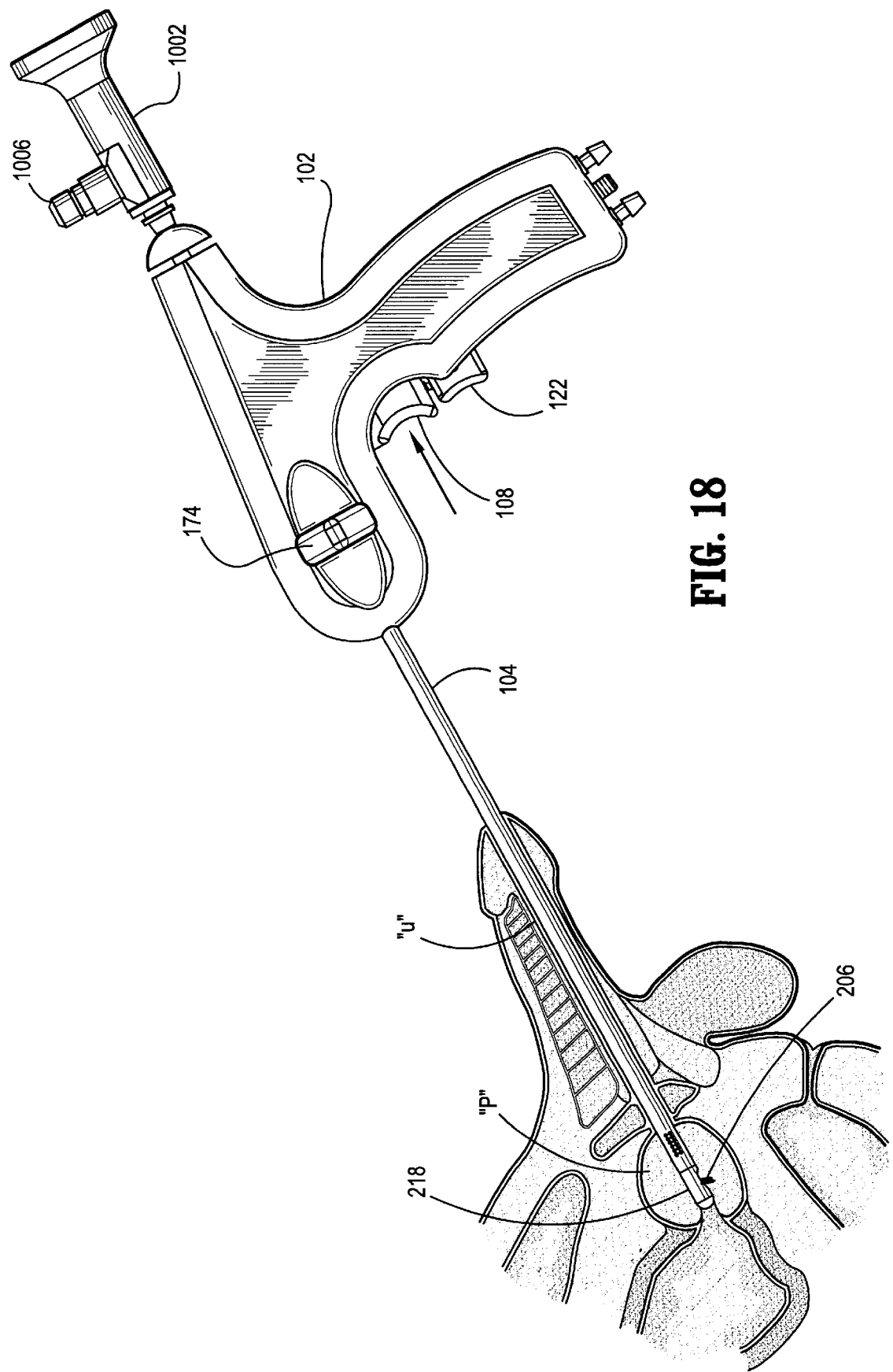

FIG. 17 is an enlarged side cross-sectional view of the handle illustrating the release trigger depressed to release the ratchet and permit retraction of the electrodes to the non-deployed position; and FIG. 18 is a view illustrating insertion of the apparatus and mounted endoscope within the urethral passage of the patient with the electrodes in the deployed position penetrating the prostatic tissue.

DETAILED DESCRIPTION OF THE PREFERRED EMBODIMENT(S)

Figure 1:
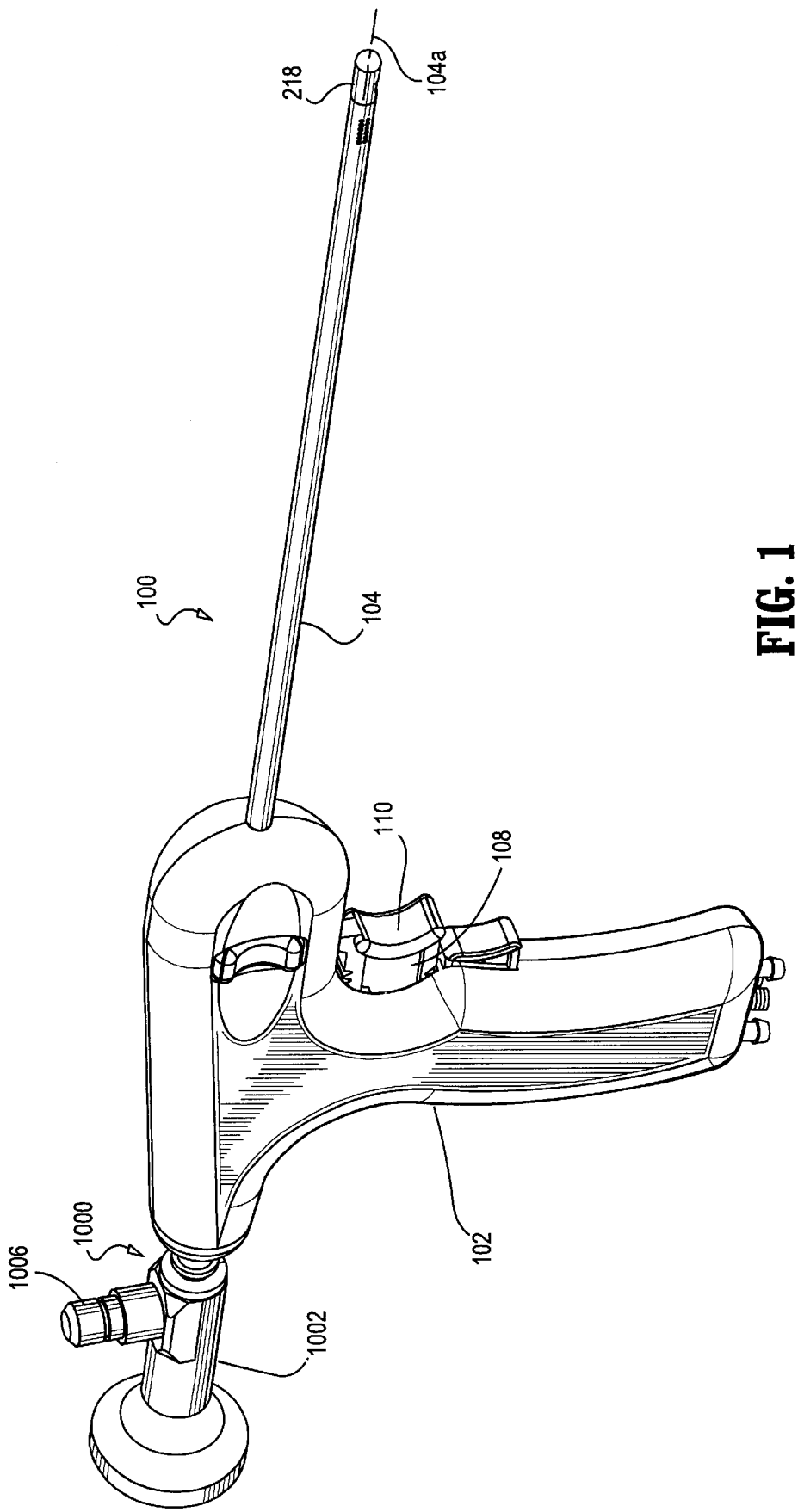
FIG. 1 is a perspective view of the thermal treatment apparatus in accordance with the principles of the present disclosure and depicting an endoscope mounted to the apparatus.

Referring now to FIG. 1, there is illustrated an apparatus 100 for delivery of electromagnetic energy to tissue for thermal treatment of the tissue including tissue ablation, tissue vaporization and/or tissue coagulation. Apparatus 100 has particular application in the treatment of benign prostate hyperplasia (BPH) with electromagnetic radio frequency (RF) energy, however, it is to be appreciated that the apparatus is not limited to such application. For example, apparatus 100 may be adapted to thermally treat prostatic tissue with microwave energy or laser energy. In addition, apparatus 100 is not necessarily limited to the treatment of BPH but may be used in other surgical procedures such as cardiac ablation, cancer treatment, etc. . . . Moreover, apparatus 100 may be used in any minimally invasive surgical procedure (e.g., endoscopic, laparoscopic, etc.) where thermal treatment of tissue is desired and access to the tissue is limited.

Generally speaking, apparatus 100 is a catheter type instrument capable of selectively and incrementally deploying a pair of RF electrodes into tissue. An RF current is transmitted from the electrodes to a grounding pad to thermally treat the tissue at a desired temperature level.

Figure 2:
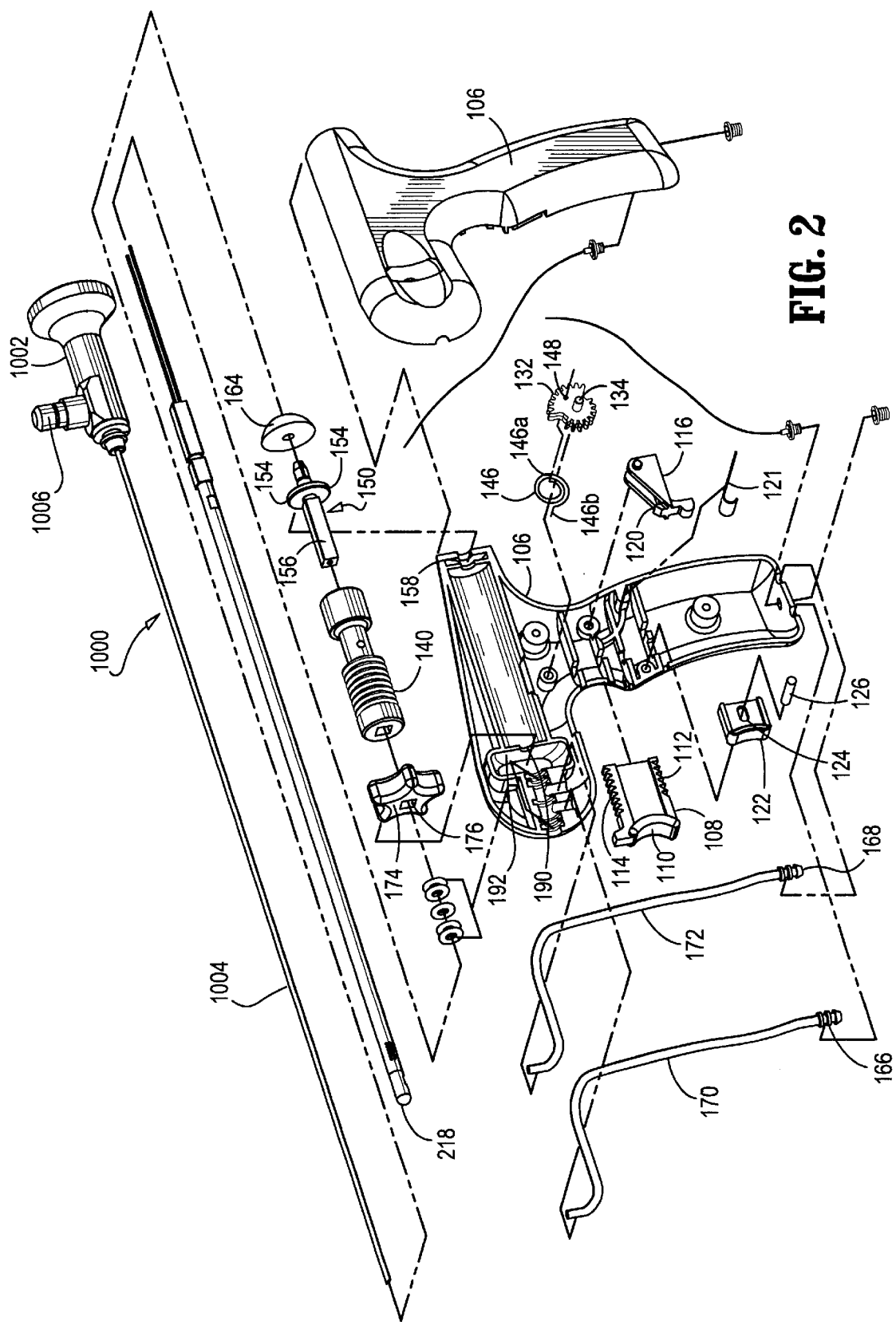
FIG. 2 is a perspective view with parts separated of the thermal treatment apparatus of FIG. 1 illustrating the components of the handle and the elongated portion.

Referring now to FIGS. 1–2, apparatus 100 is shown with an endoscope 1000 mounted thereto. Apparatus 100 includes handle 102 and elongated portion, generally identified as reference numeral 104, connected to the handle 102 and extending distally therefrom. Handle 102 includes two half sections 106 which may be connected to each other along their peripheries by suitable means including adhesives, cements, screws or the like. Handle 102 defines a pistol-type configuration to be advantageously grasped with a single hand of the surgeon and manipulated about the operative site. Handle 102 is also contoured as shown for user comfort.

Figure 3:
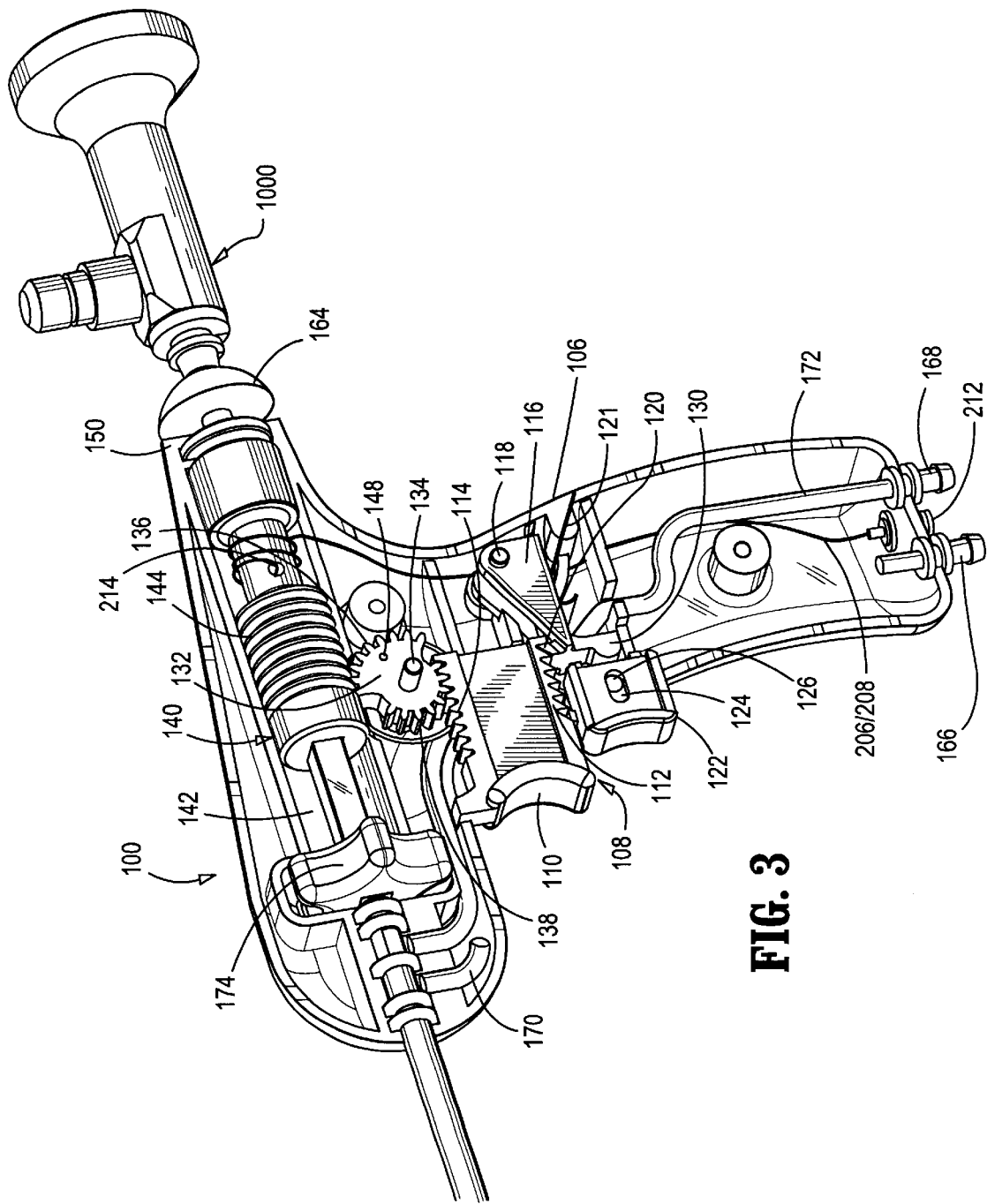
FIG. 3 is a perspective view of the handle of the apparatus of FIG. 1 with a half section of the handle removed to further illustrate the components of the handle and the mechanisms associated therewith.
Figure 4:
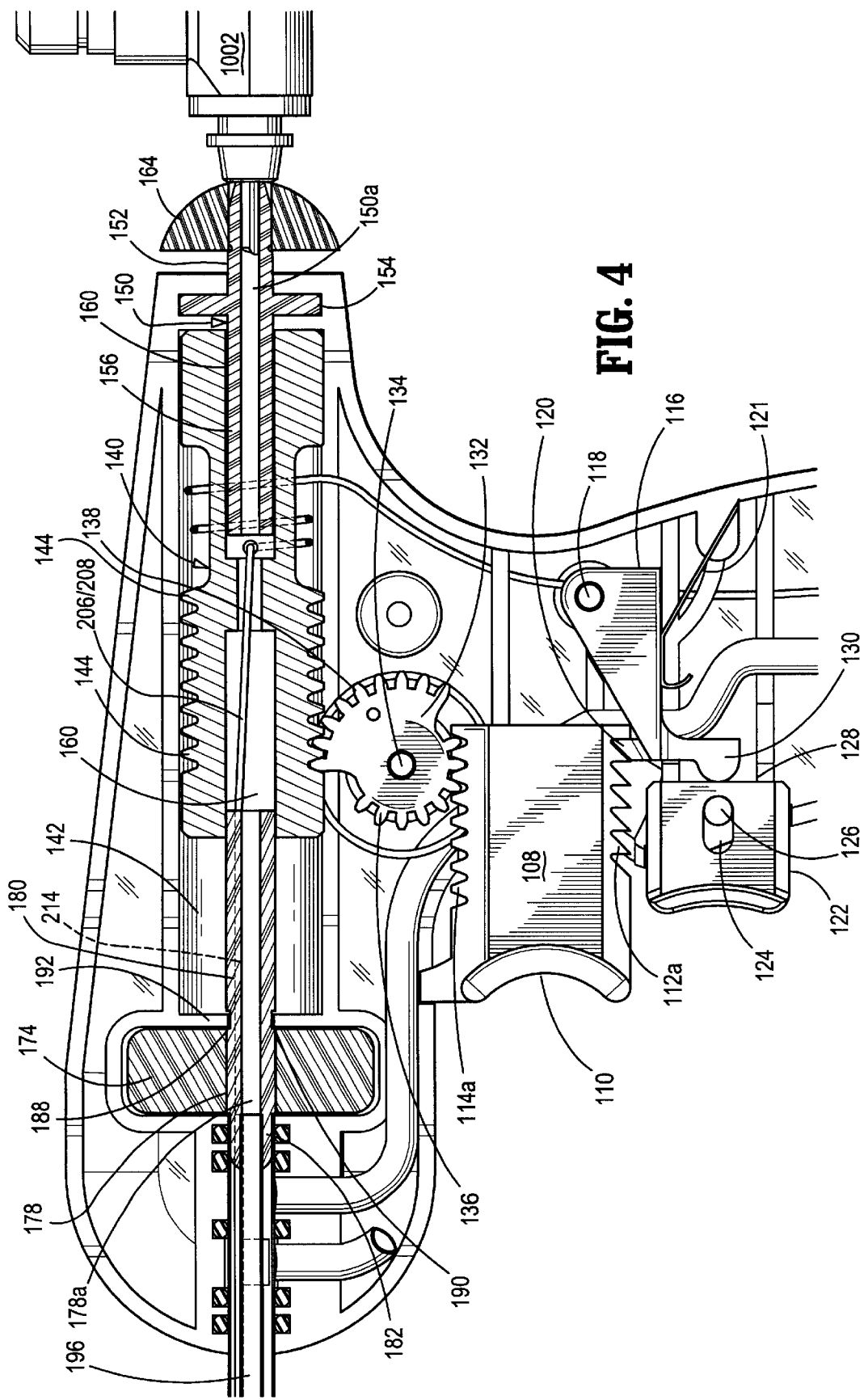
FIG. 4 is an enlarged side cross-sectional view of the handle of FIG. 3.

Referring now to FIGS. 2–4, in conjunction with FIG. 1, a drive trigger 108 is mounted to handle 102 and is longitudinally movable relative to the handle between a rest position shown in FIG. 3 and a fully depressed position to actuate the apparatus 100, i.e., to deploy the RF electrodes. Drive trigger 108 includes forward engaging surface 110 contoured for engagement by the index finger of the surgeon. The rear portion of drive trigger 108 include a lower rack 112 having engaging teeth 112a (FIG. 4) and an upper rack 114 having engaging teeth 114a. A ratchet member 116 is pivotally mounted to handle 102 about pivot pin 118 and includes engaging pawl 120 at its forward end which cooperatively engages the teeth 112a of lower rack 112 to selectively prevent drive trigger 108 from returning to its rest position when the drive trigger 108 is at least partially actuated or depressed. Thus the ratchet maintains the electrode in any number of deployed positions. A leaf spring 121 is mounted to handle 102 and abuts the lower surface of ratchet member 116 to continually bias the engaging pawl 120 into engagement with lower rack 112.

As best depicted in FIG. 4, handle 102 also includes a release trigger 122 mounted to handle 102 and reciprocally longitudinally movable to the handle 102. In a preferred embodiment, release trigger 122 includes a partial longitudinal channel 124 which receives mounting pin 126 extending from one of the half sections 106 to effect the mounting. Release trigger 122 defines a rear or proximal abutment surface 128 which engages a correspondingly positioned lower abutment portion 130 of ratchet 116 upon depression or proximal movement of the release trigger 122. Such movement of release trigger 122 causes the ratchet 116 to rotate in a counterclockwise manner thereby releasing pawl 120 from it engagement with the teeth 112a of lower rack 112 to permit drive trigger 108 to return to its initial rest position of FIG. 3.

Referring now to FIGS. 3–4, the mechanism for selectively and incrementally advancing the electrodes includes a pinion gear 132 rotatably mounted about gear pin 134 and having first and second sets of engaging teeth 136, 138 respectively. Engaging teeth 136 cooperatively interfit with teeth 114a of drive trigger 108 whereby longitudinal movement of the drive trigger 108 causes corresponding rotational movement of pinion gear 132. A drive collar 140 is slidably mounted within longitudinal bore 142 defined in handle 102 and possesses a circumferential set of teeth or grooves 144. Teeth 144 of drive collar 140 interfit with the second set of teeth 138 of pinion gear 132 such that rotational movement of the gear 132 causes drive collar 140 to longitudinally translate. As depicted in FIG. 2, a coil spring 146 is wrapped about gear pin 134 and has a first end portion 146a mounted within aperture 148 of pinion gear 132 and a second end portion 146b secured to one of half sections 106 of handle 102. Coil spring 146 normally biases pinion gear 132 in a clockwise direction (FIG. 4), thereby continually influencing drive trigger 108 to its initial rest (undepressed) condition of FIG. 4 and drive collar 140 to its retracted or proximalmost position. (FIG. 4)

A collar support 150, consisting of proximal elongated portion 152, flange 154 and distal elongated portion 156, is mounted to handle 102 by the reception of flange 154 within correspondingly dimensioned recesses 158 in each half section 106.(FIG. 3) Distal elongated portion 156 of collar support 150 is received within a correspondingly dimensioned inner bore 160 formed in drive collar 140 to support the drive collar 140 for axial movement. As shown, distal elongated portion 156 and inner bore 160 each define a rectangular cross-section. A semi-hemispherical shaped clamp 164 is mounted to proximal elongated portion 152 and functions in securing endoscope 1000 to apparatus 100 as will be described hereinbelow.

Referring still to FIGS. 2–4, apparatus 100 further includes an irrigation system for supplying irrigation fluids to the operative site for cleaning and/or cooling of the treated tissue and an aspiration system for removing fluids (i.e., irrigation and bodily) and destroyed tissue portions from the operative site. In particular, apparatus 100 includes irrigation connector 166 and aspiration connector 168, which connect to an external irrigation source (not shown) and an aspiration source (not shown) respectively. An irrigation tube 170 and an aspiration tube 172 respectively extend from irrigation connector 166 and aspiration connector 168 to endoscopic portion 104 where they are received within corresponding irrigation and aspiration ports of the endoscopic portion as will be discussed.

Handle 102 also includes a rotatable control knob 174 which serves in selectively rotating endoscopic portion 104. Control knob 174 has an aperture 176 extending therethrough and defining a rectangular cross-section.

Figure 5:
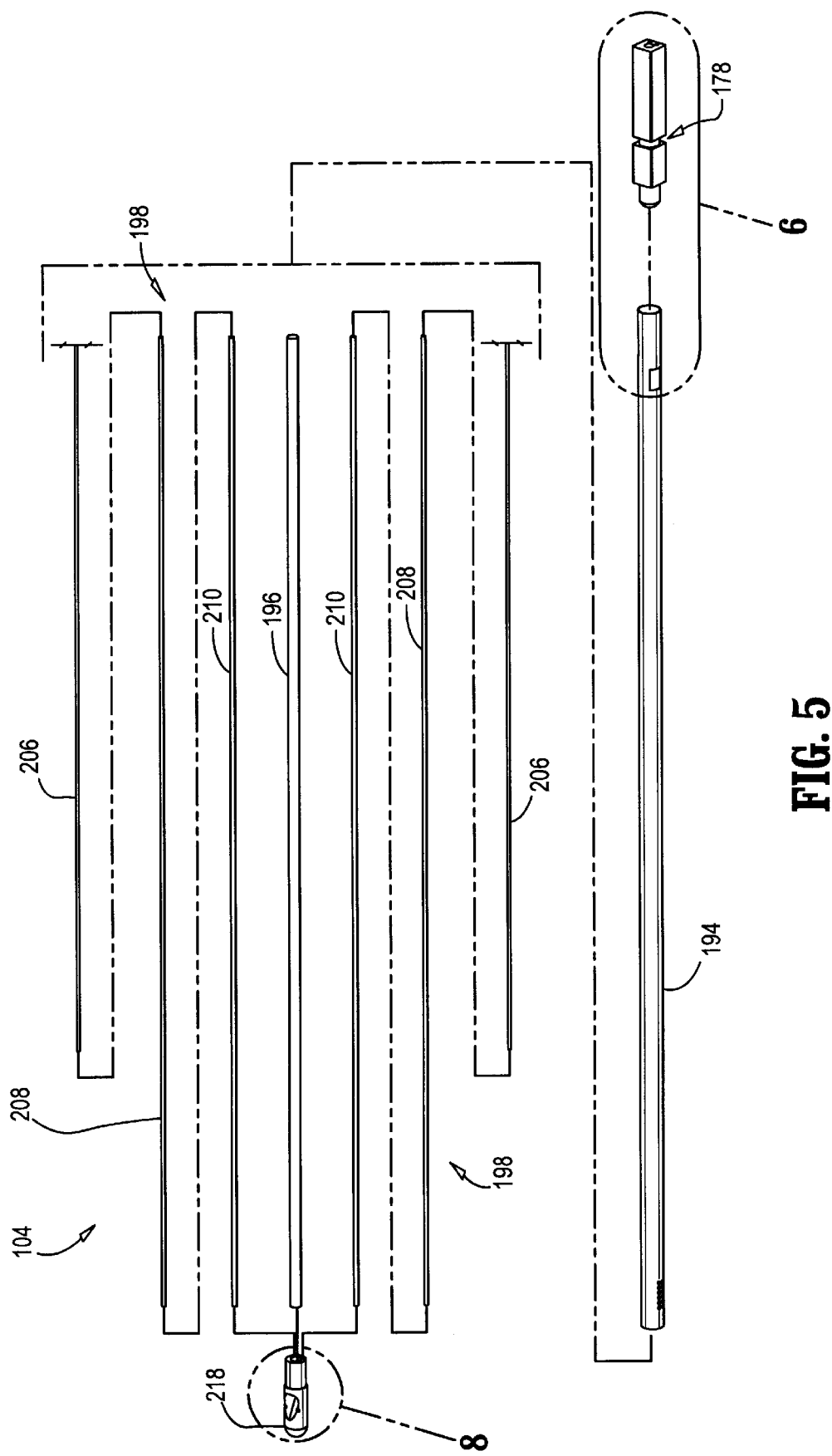
FIG. 5 is a side plan view with parts separated of the elongated portion of the apparatus illustrating the outer sleeve, the central endoscope sleeve and the two electrode units disposed within the outer sleeve.
Figure 6:
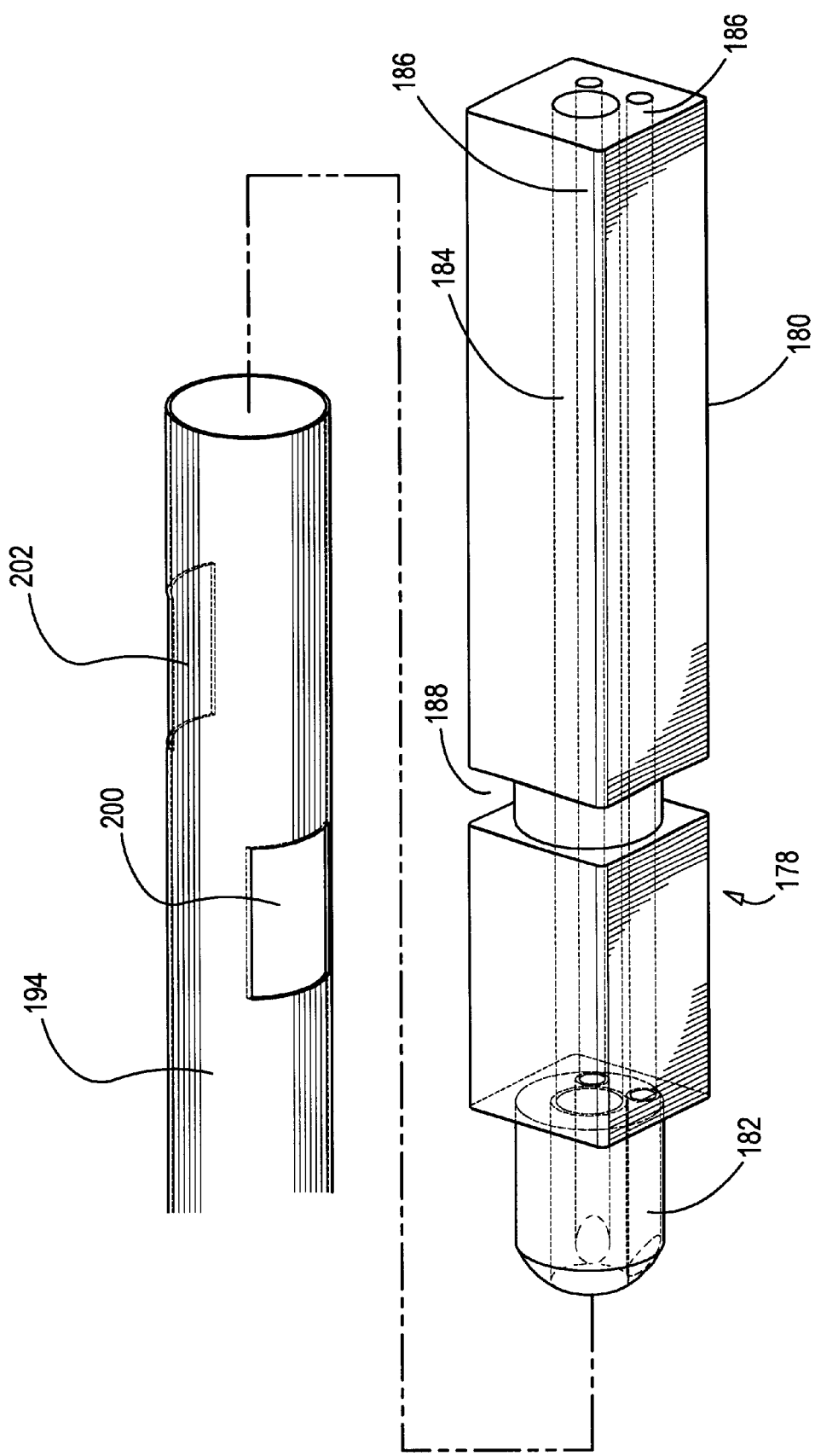
FIG. 6 is an enlarged side plan view of the proximal end of the elongated portion and the sleeve mount for mounting the elongated portion to the handle.

Referring now to FIGS. 4–6, a sleeve mount 178 is disposed in handle 102 and possesses proximal portion 180 defining a rectangular cross-section and distal portion 182. Proximal portion 180 is accommodated within rectangular-shaped aperture 176 of rotatable control knob 174 and rectangular-shaped inner bore 160 of drive collar 140. Distal portion 182 serves in mounting elongated portion 104 to handle 102 as will be discussed. Sleeve mount 178 also includes a central longitudinal bore 184 to accommodate the endoscopic portion of endoscope 1000 and two side longitudinal bores 186 which permit passage of the RF electrodes to the distal end of the apparatus 1000. As shown in FIGS. 2 and 4, a circumferential groove 188 is formed in proximal portion 180 of sleeve mount 178 and accommodates the inner portion 190 of inner mounting wall 192 to axially fix the sleeve mount 178 within handle 102.

Figure 7:
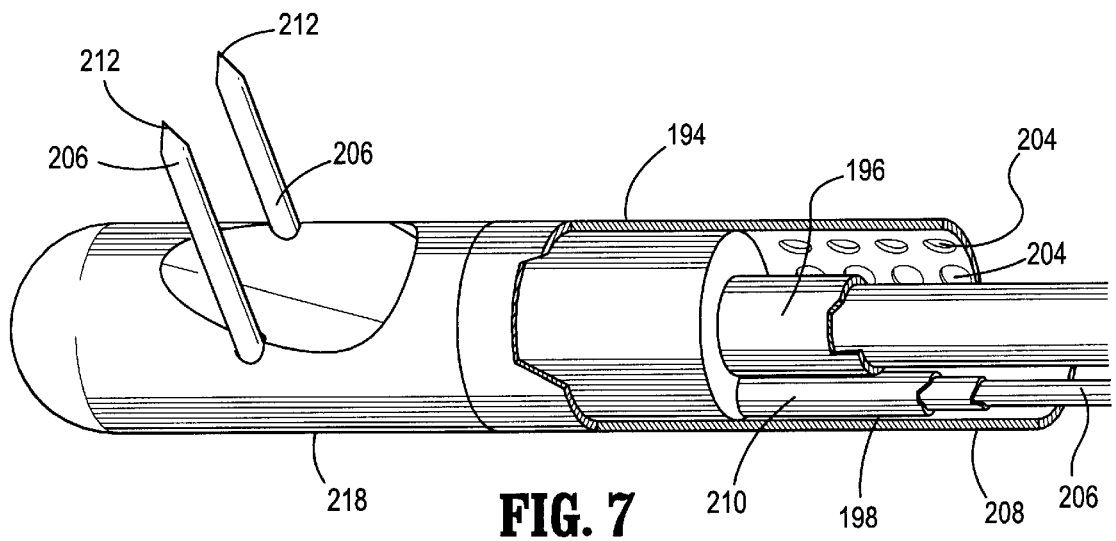
FIG. 7 is a side plan view with portions cut away of the distal end of the elongated portion and the mounted deployment tip illustrating deployment of the electrodes from the apparatus.
Figure 8:
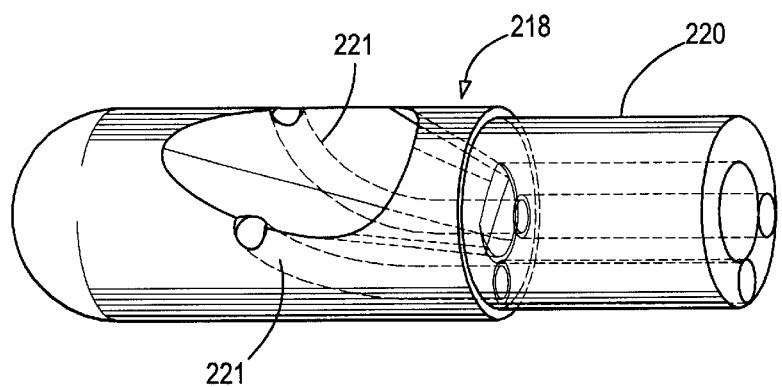
FIG. 8 is an enlarged isolated view of the distal deployment tip of the elongated portion illustrating the channels for deployment of the electrodes.
Figure 9:
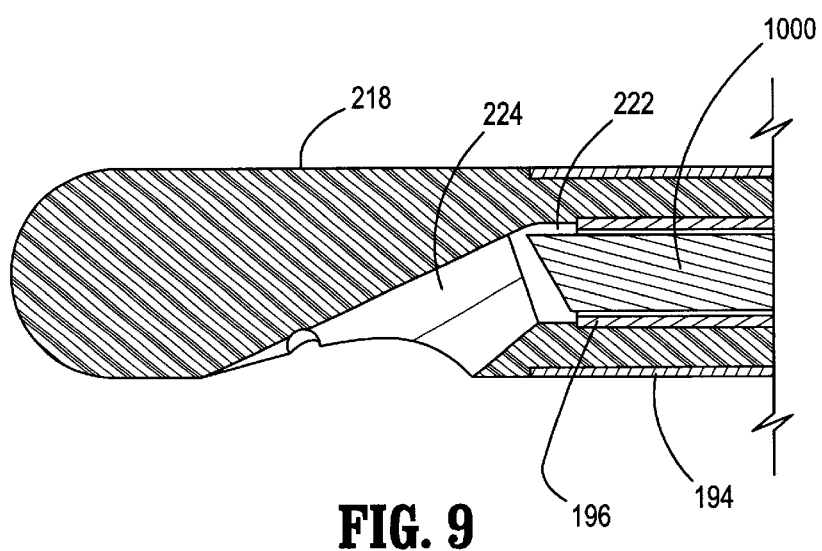
FIG. 9 is a side cross-sectional view of the deployment tip illustrating the optics channel to permit viewing of the operative site with the endoscope.

Referring now to FIGS. 5–7, in conjunction with FIGS. 1–2, endoscopic portion 104 of apparatus 100 defines a longitudinal axis 104a and has outer sleeve 194, inner scope sleeve 196 coaxially mounted within the outer sleeve 194 and two electrode units, identified generally by reference numeral 198, also mounted within outer sleeve 194. Outer sleeve 194 is mounted to handle 102 via sleeve mount 178. (FIGS. 5 and 6) In particular, distal mounting portion 182 of sleeve mount 178 is received within the correspondingly dimensioned bore of outer sleeve 194 and is secured to the outer sleeve 194 with the use of adhesives or the like. Outer sleeve 194 includes first and second apertures 200, 202 (FIG. 6) at its proximal end which receive irrigation and aspiration tubes 170, 172, respectively. Irrigation and aspiration tubes 170, 172 are preferably secured within apertures 200, 202 in fluid tight relation by any suitable means. As shown in FIG. 7, outer sleeve 178 also includes a plurality of apertures 204 at its distal end which serve as irrigation ports for dispensing irrigation fluid into the operative site and/or aspiration ports for removing fluids or destroyed tissue depending on the operative mode of the apparatus 100. The irrigation and aspiration channels of elongated portion 104 encompass the unoccupied area within outer sleeve 194.

Referring now to FIGS. 5 and 7, the electrode units 198 of apparatus 100 each include an electrode 206 which is surrounded by an insulating sleeve 208 for a major portion of its length. More specifically, insulating sleeve 208 covers the entire length of electrode 206 except for a distal end portion of the electrode which is exposed to transmit the electromagnetic RF current. Each electrode unit 198 further includes an electrode sleeve 210 which receives the electrode and insulating sleeve subassembly 206/208. Electrode sleeve 210 facilitates sliding movement of the electrode and insulating sleeve subassembly within elongated portion 104 for deployment and also isolates the subassembly from irrigation fluids within the irrigation channel of the endoscopic portion 104. Electrode sleeves 210 are each received at their proximal ends within longitudinal bores 186 (FIG. 6) of sleeve mount 178 and are preferably secured to the sleeve mount 178 with adhesives or the like.

Electrode 206 may be a thin solid wire capable of carrying an electromagnetic (RF) current and preferably has a pointed tip 212 to facilitate penetration through tissue. As depicted in FIG. 3, the electrode 206 and insulating sleeve subassembly 206/208 extends from electrical connector 212 mounted to handle 102 to drive collar 140 where it is looped several times bout the collar 140. From there, the subassembly 206/208 passes through bore 214 formed in the outer wall of drive collar 140 and extends through bore 216 of sleeve mount 104 (shown in phantom in FIG. 4) and into electrode sleeve 206 where it extends the length of the electrode sleeve 206. In FIG. 4, only one electrode and insulating sleeve subassembly 206/208 is shown. The second electrode 206 and insulating sleeve 208 unit would be routed in a similar manner.

Referring now to FIGS. 2 and 7–9, a distal deployment tip 218 is mounted to the distal end of outer sleeve 194. Deployment tip 218 preferably includes a proximal portion 220 having a reduced diameter appropriately dimensioned to be received within the bore of outer sleeve 194. Proximal portion 220 of deployment tip 218 may be secured to outer sleeve 194 with the use of adhesive or the like. Deployment tip 218 also includes two electrode deployment channels 221 which extend from the proximal end surface of the tip 218 through the side or peripheral surface thereof. Deployment channels 221 guide the electrodes 206 for deployment into the targeted body tissue. Deployment tip 218 also includes endoscope channel 222 which receives the distal end of inner scope sleeve 196. A viewing channel 224 in communication with endoscope channel 222 is also provided to permit viewing of the operative site with the endoscope 1000. The viewing channel 224 is inclined or offset relative to the longitudinal axis 104a of elongated portion 104 to permit viewing of the tissue directly treated by the side deployed electrodes 206.

Figure 10:
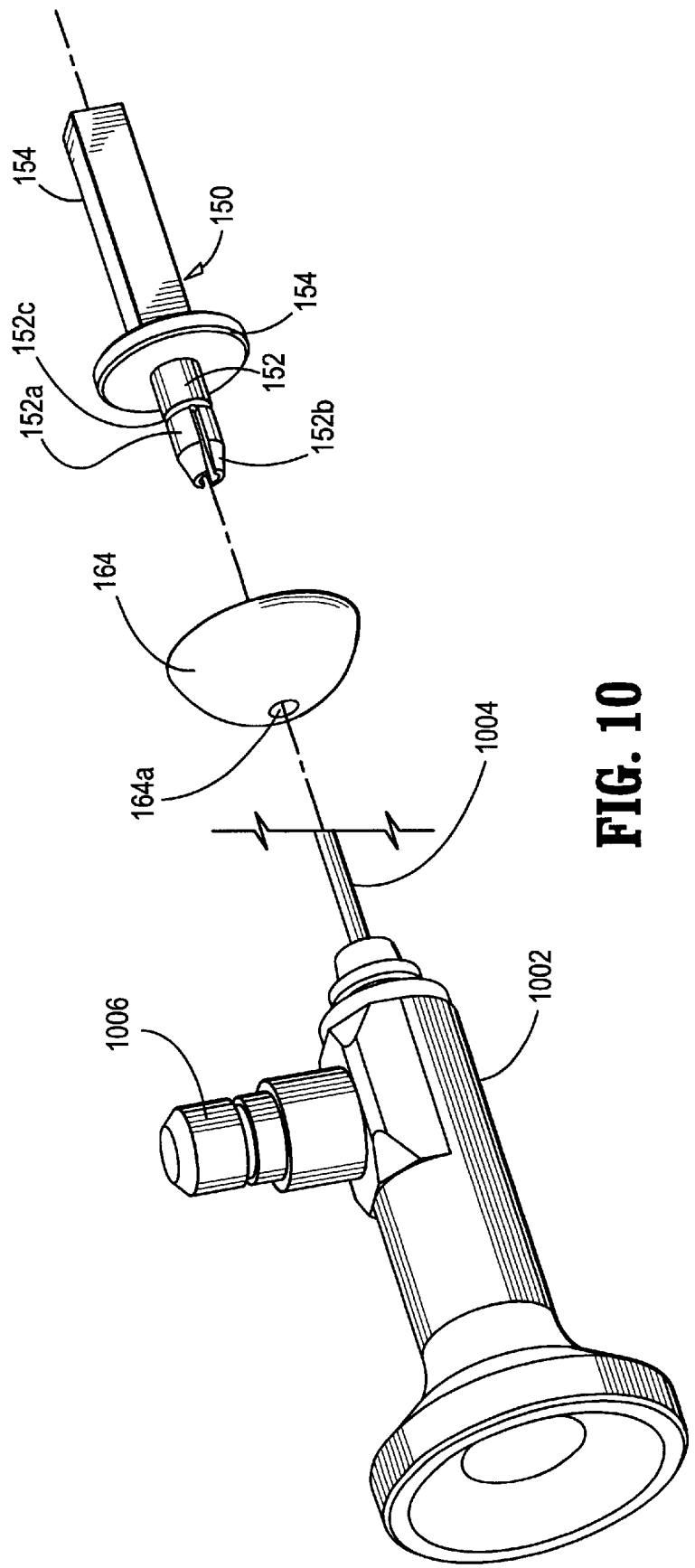
FIG. 10 is a view illustrating the mechanism for mounting the endoscope to the apparatus.

As stated above, apparatus 100 has a conventional endoscope 1000 mounted thereto. Endoscope 1000 may be any suitable endoscope used in minimally invasive surgical procedures. As depicted in FIGS. 1, 2 and 10, endoscope 1000 typically includes a frame 1002 and an endoscopic portion 1004 extending from the frame 1002. An optical system is incorporated within the scope to permit viewing of the operative site and an illumination system is also provided to illuminate the operative site. The illumination system typically consists of a plurality of optical fibers which terminate at illuminator coupler 1006. Preferably, endoscope 1000 is a side viewing or an inclined angle of view scope to permit viewing through inclined viewing channel 224 of deployment tip 218.

As stated above, apparatus 100 includes a longitudinal bore for reception and mounting of endoscope 1000. This endoscope receiving bore is best depicted in FIG. 4, and includes bore 150a of collar support 150, bore 160 of drive collar 140, central longitudinal bore 178a of sleeve mount 178 and the bore defined by inner scope sleeve 196. Endoscope 1000 is secured within the endoscope receiving bore by semi-hemispherical shaped clamp 164. As best depicted in FIGS. 4 and 10, proximal elongated portion 152 of collar support 150 extends proximally from handle 102 and includes two spaced bifurcated portions 152a, 152b. Clamp 164 slides over bifurcated portions 152a, 152b (i.e., the bifurcated portions 152a, 152b are received within bore 164a of clamp 164) whereby upon positioning thereof the bifurcated portions 152a, 152b are displaced radially inwardly to clamp down on the endoscopic portion 102 of endoscope 1000 thus retaining the scope 1000 at a fixed longitudinal position relative to the apparatus 100. Preferably bore 164a of clamp 164 is appropriately dimensioned to cause sufficient inward radial displacement of the bifurcated portions 152a, 152b to establish a frictional engaged relation with the endoscopic portion 1004. Proximal elongated portion 152 may include a circumferential locking groove 152c to secure the clamp 164 on collar support 150.

Operation of the Apparatus

The operation of the apparatus will be now be discussed. The apparatus 100 in its non-actuated position of FIG. 1 and with endoscope 1000 mounted thereto is positioned such that distal deployment tip 218 is adjacent the tissue to be thermally treated. Thereafter, the surgeon depresses drive trigger 108. With reference to FIG. 11, as drive trigger 108 moves proximally, pinion gear 132 rotates in a counter clockwise direction through the interengagement of ratchet teeth 114a of the drive trigger 108 and teeth 136 of the pinion gear. This movement causes drive collar 140 to translate distally through the interengagement of teeth 138 of pinion gear 132 and circumferential teeth 144 of the drive collar 140. As drive collar 140 advances, the electrode and insulating sleeve units 206/208 are advanced through electrode sleeves 210 to at least partially deploy electrodes 206 as shown in FIG. 12. It is to be appreciated that the ratchet mechanism including ratchet 116 and lower rack 112 of drive trigger 108 provides for selective controlled and incremental movement of drive collar 140 to selectively and incrementally control the level of deployment of electrodes 206 from deployment tip 218. Thus, the surgeon is capable of selectively adjusting the heating pattern of the electrodes, as well as the intensity of the heating pattern by the selective depression of drive trigger 108. It is also to be noted that the return movement of pawl 120 subsequent to clearing each single tooth 112a of lower rack 112 provides a perceptible tactile and audible indicator to the user that drive trigger 108 has been depressed for a predetermined distance and, accordingly, drive collar 140 has been advanced a predetermined distance. Thus, the operator can selectively and incrementally control the axial advancement of drive collar 140 and thus the level of deployment of electrodes 206 from deployment tip 218 by tactilely and/or audibly monitoring the number of clicks which correspond to each return of pawl 120 to the engaged position. In addition, ratchet 116 prevents the movement of trigger 108 to its initial position subsequent to at least partial depressing movement of the trigger 108 thereby preventing drive collar 140 from moving in the proximal direction. As a result, the electrodes 206 are retained at a predetermined measure of deployment and are incapable of moving in the proximal direction until ratchet 116 is released via depression of release trigger 122.

At this point in the procedure, i.e., with electrodes 206 partially deployed as shown in FIG. 12 and penetrating the targeted tissue, apparatus 106 may be energized whereby an RF current is transmitted from the exposed electrode 206 to thermally treat the tissue over a predetermined area. If a larger treating pattern or area is desired during the procedure, the electrodes 206 may be advanced to their fully deployed position depicted in FIGS. 13 and 14 by continued depressive engagement with drive trigger 108. At all points during the procedure, the thermally treated tissue can be monitored with endoscope 1000.

Figure 15:
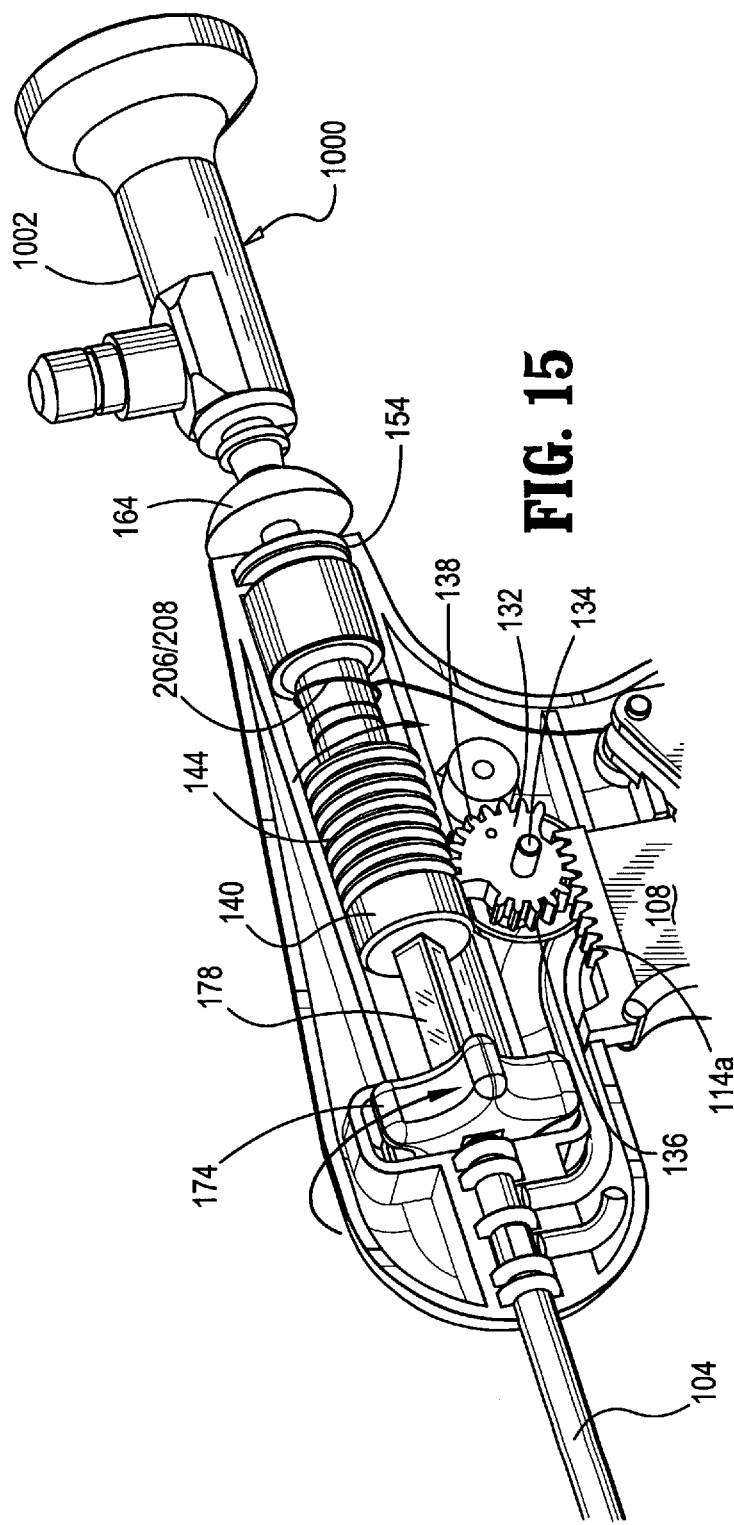
FIG. 15 is a perspective view of the handle illustrating the mechanism for imparting rotational movement to the elongated portion.
Figure 16:
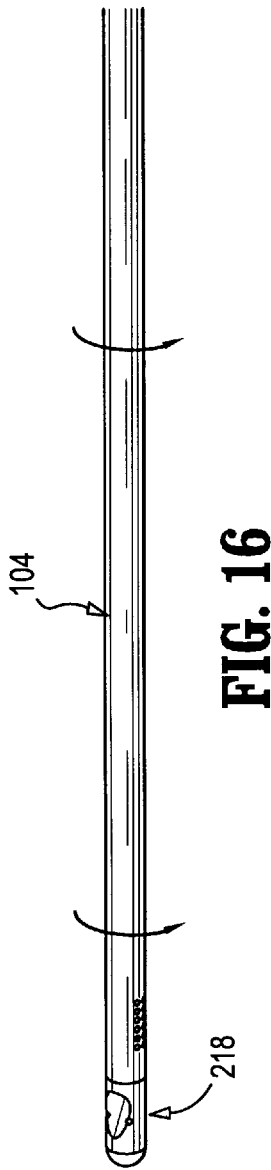
FIG. 16 is a side plan view of the endoscopic portion illustrating rotational movement of the elongated portion.

In addition, during the surgical procedure, the orientation of electrodes 206 relative to the longitudinal axis of the elongated portion 104 may be controlled by rotation of control knob 174. As best depicted in FIGS. 15–16, rotation of control knob 174 causes sleeve mount 178 to rotate thereby causing rotational movement of elongated portion 104 (i.e., outer sleeve 194, inner scope sleeve 196 and electrode sleeves 210 which are all fixedly secured to the sleeve mount 178) and deployment tip 218. Drive collar 140 rotates as well as permitted by circumferential arrangement of teeth 144. Preferably, electrodes 206 are in their non-deployed position prior to rotating control knob 174.

Upon completion of the thermal treatment, the apparatus is deactivated and electrodes 206 are returned to their non-deployed position. With reference to FIG. 17, return of the electrodes 206 is effected by depression of release trigger 122 which causes pawl 116 to pivot in a counterclockwise direction through engagement of proximal abutment surface 128 with lower abutment portion 130 of ratchet 116 thereby releasing pawl 120 from its engagement with teeth 112*a* of drive trigger 108 to permit the drive trigger 108 and drive collar 140 to return to their initial position under the influence of coil spring 146 (FIG. 2). In particular, with pawl 120 released, pinion gear 132 rotates in a clockwise direction as influenced by coil spring 146 to cause drive collar 140 to move proximally and drive trigger 108 distally to their respective initial positions.

Referring now to FIG. 19, apparatus 100 is illustrated in conjunction with the thermal treatment of the prostate to alleviate the symptoms of BPH (hyperplasia) in treating BPH. Apparatus 100 in its non-activated condition is inserted through the urethral passage "u" and advanced until deployment tip 218 is adjacent the prostate gland "p". The orientation of elongated portion 104 is adjusted via control knob 174 as appropriate. Drive trigger 108 is depressed to deploy the electrodes 206 whereby upon deployment the penetrating end portions 212 of the electrodes 206 pierce the urethral wall and enter into the prostate tissue.

The apparatus 100 is energized to thermally treat (e.g., ablate, valorize or cauterize) the desired prostatic tissue with RF energy. As a result of this treatment, the prostatic tissue dies and necroses, thus, relieving pressure off of the urethral wall and alleviating the symptoms of BPH. The entire treatment may be viewed with endoscope 1000. In addition, the irrigation and aspirating capabilities of apparatus 100 may be utilized as appropriate to cool and/or flush away tissue (irrigation) and remove excess fluids and/or tissue (aspiration).

Apparatus 100 provides many advantages in the thermal treatment of body tissue, particularly, the prostatic tissue. The pistol configuration of the handle and associated drive trigger and release trigger mechanisms and ratchet enables the surgeon to operate the apparatus with a single hand, thus, freeing the other hand to perform other surgical functions. The selective and controlled deployment of the electrodes facilitates the formation of the desired heating pattern which, consequently, results in thermal treatment of the appropriate diseased tissue while reducing the amount of damage to the healthy tissue. In addition, the rotatable control knob 174 enhances placement of the electrodes 206 within the tissue.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. The device for thermal treatment of tissue, wherein the electrode unit includes an electrode and an insulation sleeve concentrically positioned over the electrode.

2. The device for thermal treatment of tissue of claim 1, wherein including a second insulation sleeve fixedly positioned in the annular channel and accommodating the electrode, wherein the second insulation sleeve isolates the electrode unit from aspiration and irrigation.

3. The device for thermal treatment of tissue of claim 2, wherein the electrode unit is adapted to slide within the second insulation sleeve.

4. The device for thermal treatment of tissue of claim 1, including a deployment tip connected to the distal end of the outer sleeve.

5. The device for thermal treatment of tissue of claim 4, wherein the deployment tip includes at least one deployment channel dimensioned to permit passage of the electrode unit therein.

6. A device for the thermal treatment of tissue, which comprises:
a handle;
an endoscopic portion connected to the handle, the endoscopic portion including:
an outer sleeve defining a proximal end and a distal end and a central longitudinal axis, the distal end of the outer sleeve defining a plurality of apertures;
an inner scope sleeve concentrically positioned within the outer sleeve, the outer sleeve and the inner scope sleeve defining an annular channel therebetween in fluid communication with the apertures in the distal end of the outer sleeve, wherein the channel functions to alternately provide aspiration and irrigation through the apertures; and
at least one electrode unit at least partially positioned within the annular channel, the electrode unit having an electrode with a penetrating distal end and a proximal end connectable to an electrical source;
at least one fluid conveying connector mounted to the handle and in fluid communication with the annular channel and the plurality of apertures, the one fluid conveying connector in fluid communication with a source of irrigation and aspiration to alternately provide irrigation and aspiration; and
a drive trigger mounted on the handle for positioning the electrode unit between a first non-deployed position and a second deployed position.

7. The device for thermal treatment of tissue of claim 6, wherein the trigger is slidably movable in a general longitudinal direction with respect to the longitudinal axis to selectively and incrementally move the one electrode unit between the non-deployed position and the fully deployed position.

8. The device for thermal treatment of tissue of claim 7, wherein the handle includes a ratchet mechanism for permitting movement of the trigger in one direction corresponding to movement of the one electrode to the fully deployed position while preventing movement of the trigger in a second longitudinal direction.

9. A device for the thermal treatment of tissue, which comprises:
a handle;
an endoscopic portion connected to the handle, the endoscopic portion including:
an outer sleeve defining a proximal end and a distal end and a central longitudinal axis;
an inner scope sleeve concentrically positioned within the outer sleeve, the outer sleeve and the inner scope sleeve defining an annular channel therebetween; and
at least one electrode unit at least partially positioned within the annular channel, the electrode unit having an electrode with a penetrating distal end and a proximal end connectable to an electrical source;

at least one fluid conveying connector mounted to the handle and in fluid communication with the annular channel, the one fluid conveying connector in fluid communication with a source of irrigation and aspiration to alternately provide irrigation and aspiration;

a drive trigger mounted to the handle for positioning the one electrode unit between a first non-deployed position to a second deployed position, wherein the drive trigger is slidably movable in a general longitudinal direction with respect to the longitudinal axis to selectively and incrementally move the one electrode unit between the non-deployed position and the fully deployed position;

a ratchet mechanism positioned in the handle for permitting movement of the drive trigger in one direction corresponding to movement of the one electrode unit to the fully deployed position while preventing movement of the drive trigger in a second longitudinal direction; and a manually engageable ratchet release trigger mounted to the handle and operatively connected to the ratchet mechanism, the ratchet release trigger slidably mounted relative to the handle and positioned adjacent the drive trigger, the release trigger adapted to move in a general longitudinal direction with respect to the longitudinal axis to release the ratchet mechanism to permit movement of the drive trigger in the second longitudinal direction corresponding to movement of the one electrode unit to the non-deployed position.

10. The device for thermal treatment of tissue of claim 9, including a rack and pinion mechanism associated with the drive trigger for selectively moving the one electrode unit.

11. The device for thermal treatment of tissue of claim 9, wherein the endoscopic portion is rotatable about the central longitudinal axis to position the one electrode unit at a predetermined angular orientation with respect to the longitudinal axis.

12. The device for thermal treatment of tissue of claim 9, wherein the endoscopic portion includes an endoscope received within the inner scope sleeve for viewing tissue treated by the one electrode unit.

13. The device for thermal treatment of tissue of claim 9, wherein the handle includes a rotatable control knob operatively connected to the endoscopic portion, the rotatable control knob rotatable to impart corresponding rotational movement to the endoscopic portion.

14. The device for thermal treatment of tissue of claim 9, wherein the handle is configured and dimensioned to be gripped by a single hand of a surgeon, the handle defining a pistol grip configuration.

15. The device for thermal treatment of tissue of claim 9 further including one of a source of irrigation and a source of aspiration connected to the one fluid conveying connector.

16. The device for thermal treatment of tissue of claim 15 including first and second fluid conveying connectors, the first and second connectors adapted for connection to a source of irrigation and a source of aspiration respectively.

17. The apparatus according to claim 19 further including an elongate inner member disposed within the outer member, wherein the fluid channel is defined between the inner member and the outer member.

18. The apparatus according to claim 17 wherein the outer member includes an aperture in a side wall thereof, the aperture being the fluid port.

19. The apparatus according to claim 18 wherein the side wall of the outer member includes a plurality of apertures thereby defining a plurality of fluid ports.

20. The apparatus according to claim 17 wherein the inner member is coaxially arranged within the outer member whereby the fluid channel is annular in configuration.

21. The apparatus according to claim 16 including first and second fluid connectors, the first and second connectors adapted for connection to a source of irrigation and a source of aspiration respectively.

22. The apparatus according to claim 21 including a source of irrigation connected to the first connector and a source of irrigation connected to the second connector.

23. The apparatus according to claim 16 wherein the one electrode is a radiofrequency electrode.

24. The apparatus according to claim 17 including a second sleeve mounted within the fluid channel, the one electrode being disposed within the second sleeve.

\* \* \* \* \*